United States Patent
Roser et al.

(10) Patent No.: US 6,190,701 B1
(45) Date of Patent: Feb. 20, 2001

(54) COMPOSITION AND METHOD FOR STABLE INJECTABLE LIQUIDS

(75) Inventors: Bruce Joseph Roser; Arcadio Garcia De Castro, both of Cambridge (GB); James Maki, Deerfield, IL (US)

(73) Assignee: Peter M. Ronai, Salem, OR (US)

( * ) Notice: Under 35 U.S.C. 154(b), the term of this patent shall be extended for 0 days.

(21) Appl. No.: 09/271,204

(22) Filed: Mar. 17, 1999

(51) Int. Cl.[7] ............................. A61K 9/50; B32B 15/16
(52) U.S. Cl. .................... 424/499; 424/501; 424/502; 428/402.21
(58) Field of Search ................... 424/499, 501, 424/502; 428/402.21

(56) References Cited

U.S. PATENT DOCUMENTS

| | | | |
|---|---|---|---|
| 3,996,355 | 12/1976 | Lin et al. | 424/228 |
| 4,891,319 | 1/1990 | Roser | 435/188 |
| 5,126,123 | 6/1992 | Johnson | 424/45 |
| 5,589,167 | 12/1996 | Cleland et al. | 424/85.7 |
| 5,770,181 | 6/1998 | Kirkland | 424/9.37 |

FOREIGN PATENT DOCUMENTS

| | | |
|---|---|---|
| 21871991 | 9/1987 | (GB) . |
| 9820689 | 9/1998 | (GB) . |
| WO91/18091 | 11/1991 | (WO) . |
| WO97/48485 | 12/1997 | (WO) . |
| WO98/41188 | 9/1998 | (WO) . |

OTHER PUBLICATIONS

Jodar et al, Genetic Eng. News, "Revolutionizing Immunizations", Feb. 15, 1998, pp. 1–5.
Lloyd et al, Global Program on Vaccines . . . , "Pre–Filled Monodose Injection Devices . . . ", May 1998, pp. 1–23.
Powderject Press Release, Powederject's Hepatitis BDNA Vaccine First to Successfully . . . , Jan. 25, 1999, pp. 1–2.
Krafft et al, Biochimie, vol. 80, "Highly fluorinated amphiphile and collodial systems, and their . . . ", 1998, pp. 489–514.
WHO Global Programme on Vaccines and Immunizations (GPV), Aug. 6, 1997, pp. 1–8.
Green et al, J. Phys. Chem. vol. 93, "Phase Relations and Vitrification in Saccharide–Water . . . ", 1989, pp. 2880–2882.
Geyer et al, Organ Perfusion and Preservation, "Survival of Rats Totally Perfused with a . . . ", 1968, pp. 85–95.

*Primary Examiner*—Carlos Azpuru
(74) *Attorney, Agent, or Firm*—Jacobson, Price, Holman & Stern, PLLC

(57) ABSTRACT

A composition for delivering a stable, bioactive compound to a subject comprising a first component and a second component, the first component comprises microparticles of sugar glass or a phosphate glass containing the bioactive agent. The sugar glass or phosphate glass optionally includes a glass formation facilitator compound, and the second component comprises at least one biocompatible liquid perfluorocarbon in which the first component is insoluble and dispersed. The liquid perfluorocarbon optionally includes a surfactant.

18 Claims, 1 Drawing Sheet

Alkaline Phosphatase in Mannitol, Calcium Lactate & Byco C glass at 55°C

Immunogenicity in Guinea Pigs of Stablished, Dried Tetanus Toxoid

COMPOSITION AND METHOD FOR STABLE INJECTABLE LIQUIDS

BACKGROUND OF THE INVENTION

Vaccines or drugs in solution ready for injection are inherently unstable and need refrigeration. The pharmaceutical industry has traditionally tackled the instability problem by freeze-drying drugs. This is expensive, inconvenient and inherently dangerous, since incorrect reconstitution of dried drugs can result in wrong doses or contaminated solutions. Many attempts have been made over the past 100 years to develop robust, stable, ready-to-inject liquid formulations with pitiful lack of success. Only inherently tough small molecule drugs can survive in aqueous solution with a useful shelf life.

This problem is particularly acute in the vaccine industry. By the year 2005 it is estimated that 3.6 billion doses of vaccine will have to be administered world-wide. It has been stated by the World Health Organization (WHO) that this will not be possible using standard vaccine formats which need to be refrigerated at all times ("Revolutionizing Immunizations." Jodar L., Aguado T., Lloyd J. and Lambert P-H. Genetic Engineering News Feb. 15, 1998). A "cold chain" of refrigerators is currently in use, which stretches from the vaccine factories to provincial towns in the developing world. The cost of the cold chain for the vaccine industry and for non-governmental health organizations running immunization campaigns is enormous. The WHO has estimated that just the maintenance cost of the cold chain is over $US 200 million annually. In addition, immunization campaigns may reach only those living close to the last link of the cold chain.

Vaccination campaigns require medically trained staff to ensure that the dose is correctly injected and shows no signs of degradation. The need to reconstitute some vaccines, such as measles, yellow fever and BCG, in the field is also a serious concern. This must be done precisely to ensure correct dosage and it also introduces a potential source of contamination, which has frequently led to clinical disasters. In addition, it is often necessary to give more than one vaccine at a session and this may require multiple injections, as particular mixtures or "multivalent" vaccines may not be available due to the chemical incompatibility of some of the components. The WHO has highlighted these problems by actively encouraging research into the next generation of stable vaccines which have no need for refrigeration and which need no reconstitution ("Pre-Filled Monodose Injection Devices: A safety standard for new vaccines, or a revolution in the delivery of immunizations?" Lloyd J. and Aguado M. T. WHO publication May 1998. "General policy issues: injectable solid vaccines: a role in future immunization?" Aguado M. T., Jódar L., Lloyd J., Lambert P. H. WHO publication No A59781.)

An ideal solution to this problem would be completely stable, ready-to-inject formulations. Such stable vaccines could be packed as individual doses in an injecting device itself, or, for mass immunization campaigns, shipped in larger volumes and administered by means of a needle-free jet injector. The transdermal delivery of dry solids by gas jet injection has been described (Sarphie D F, Burkoth T L. Method for providing dense particle compositions for use in transdermal particle delivery. PCT Pub No. WO 9748485 (1996)) and transdermal vaccination with dry DNA vaccines is apparently very effective ("Powderject's Hepatitis B DNA Vaccine First To Successfully Elicit Protective Immune Response In Humans" at http://www.powderject.com/ pressreleases.htm (1998)).

The hypersonic shockwave of helium gas that is used to drive these powder injectors has a limited power and cannot deliver its dose of fine particles intra-muscularly. This is because the low-mass particles cannot achieve adequate momentum for deep penetration. While the intradermal delivery of DNA vaccines coated on to colloidal gold particles is adequate for good immunogenicity, the common vaccines, adjuvanted with insoluble aluminum or calcium salts, induce unacceptable skin irritation. They must be given intramuscularly. What is required is a flexible system capable of a range of delivery depths, from intradermal to deep intramuscular, similar to that achievable by existing needle and syringe technology. For mass vaccination campaigns this has been solved by the development of the liquid jet injector capable of accelerating a narrow (~0.15 mm diameter) stream of liquid, using pressures of around 3,000 psi, into a "liquid nail". This device delivers its dose painlessly through the skin into the deep subcutaneous or muscle tissue by punching a minute hole through the epidermis. The high momentum imparted to the liquid stream ensures deep penetration. To date, the injected drugs and vaccines have been water-based but because of the instability problems discussed above, the range of stable aqueous products accessible to this technology is very limited.

It is now recognized that a wide range of bioactive molecules may be stabilized by drying in sugar glasses (Roser B. "Protection of proteins and the like" UK patent No 2,187,191. Roser B and Colaco C. "Stabilization of biological macro-molecular substances and other organic compounds" PCT Pub No WO 91/18091. Roser B. and Sen S. "New stabilizing glasses". PCT patent Application no: 9805699.7. 1998). These dry, stabilized actives are unaffected by hostile environments such as high temperatures and ionizing radiation.

The mechanism underlying the remarkable stabilization of molecules by sugars is glass-transformation. As the sugar solution containing an active molecule is dried, it can either crystallize when the solubility limit of the sugar is reached, or can become a supersaturated syrup. The ability of the sugar to resist crystallization is a crucial property of a good stabilizer. Trehalose is good at this (Green J L. & Angel C A. Phase relations and vitrification in saccharide water solutions and the trehalose anomaly J. Phys. Chem. 93 2880–2882 (1989)) but not unique. Further drying progressively solidifies the syrup, which turns into a glass at a low residual water content. Imperceptibly, the active molecules change from liquid solution in the water to solid solution in the dry sugar glass. Chemical diffusion is negligible in a glass and therefore chemical reactions virtually cease. Since denaturation is a chemical change it cannot occur in the glass and the molecules are stabilized. In this form the molecules can remain unchanged providing one other condition is met. This is the second crucial property of a good stabilizer viz. that it is chemically inert and non-reactive. Many glasses fail because they react with the product on storage. Obvious problems occur with reducing sugars, which may form good physical glasses but then their aldehyde groups attack amino groups on the products in a typical Maillard reaction. This is the main reason that many freeze-dried pharmaceuticals require refrigerated storage. Non-reactive sugars give stable products, which require no refrigeration at all.

Biomolecules immobilized in sugar glass are also stable in non-aqueous industrial solvents in which they themselves and the sugar are both insoluble (Cleland J L. and Jones A J S. "Excipient stabilization of polypeptides treated with organic solvents" U.S. Pat. No. 5,589,167. (1994)). Since the sugar glass acts as an impermeable barrier in a non-solvent liquid, the biomolecules in solid solution in the glass are protected both from the chemical reactivity of the solvent and from the environment. Providing the liquid itself is stable, sensitive products in suspended glass particles constitute a stable two phase liquid formulation. Industrial solvents of the kind described by Cleland and Jones (1994) have a limited utility in processing. Substituting a biocompatible non-aqueous liquid would enable stable liquid formulations of even the most unstable drugs, vaccines and diagnostics to be formulated.

The first generation of stable non-aqueous liquids designed to be used in drug or vaccine delivery (B. J. Roser and S. D. Sen "Stable particle in liquid formulations". PCT Patent Application no. GB98/00817 described formulations of powders of stabilizing glasses containing the active, suspended in injectable oils such as sesame, arachis or soya oil or simple esters such as ethyl oleate. The suspended sugar glass particles are of an intensely hydrophilic nature while the oils are hydrophobic. Because of the strong tendency of the hydrophilic and hydrophobic phases to separate, the sugar glass particles tended to clump together. In order to stabilize such "water in oil" type suspensions the use of oil-soluble surfactants dissolved in the continuous oil phase was often required.

These low HLB (Hydrophilic/Lipophilic Balance) surfactants accumulate at the interface between the hydrophilic particles and the oil and coat them with an amphiphilic layer which is more compatible with the continuous oil phase. Because each sugar glass particle is separated from its neighbors by dry oil, no chemical interaction can go on between particles. It is therefore possible to have several different populations of particles, each containing a different potentially interactive molecule, in the same oil preparation, without them being able to interact. Complex multivalent vaccines can be produced in this way.

However, this approach has been subsequently found to have certain drawbacks that prevent it from being a universal solution. These include the inevitable sedimentation of the suspended particles, which have a typical density around 1.5 g/cm$^3$, in the less dense, oily vehicle. The patent acknowledges this problem and aims to solve it by reducing the particle size to below 1 $\mu$m in diameter in order for them to remain suspended by thermodynamic forces such as Brownian motion. The requirement for all particles to be below 1 $\mu$m in diameter is a disadvantage of the proposed formulations. Achieving such small particle powders is by no means an easy task. Improved spray drier designs may be able to achieve this but the small particle size would prevent the use of cyclone type collectors and require a system of filters for product recovery.

Reducing particles to sub-micron size may also, in theory, be achieved after the particles are suspended in the oil, with high-pressure micro-homogenizing equipment such as the Microfluidizer (Constant Systems Inc.). This involves an extra step to the process and we have found it not to be very efficient in breaking down spray-dried sugar glass microspheres, which have very high mechanical strength because of their spherical shape. This mandates multiple passes through the equipment. Even then, this tends to leave a number of the larger particles untouched and therefore would require a subsequent filtration or sedimentation step to remove them. Also, the high viscosity of the suspensions in the usual oily vehicles makes them difficult both to draw up into the syringe and requires that they be injected slowly. It precludes fast flows through fine nozzles such as are experienced in a liquid jet injector system.

It has also been found that particles suspended in an oil, specially when containing a low HLB surfactant, are difficult to extract subsequently into an aqueous environment because, surprisingly, they maintain a tightly bound, water repellent coat of oil around them, even after washing in aqueous buffer. They therefore require very vigorous shaking and mixing or the addition of yet more water-soluble detergent (this time with a high HLB) for the particles to leave the oil phase and enter the water phase. This becomes more of a problem as the particle size is reduced. The final outcome is often a rather messy mixed emulsion rather than two cleanly separate phases. In the body this problem can cause slow and unpredictable release of the active rather than the prompt and predictable delivery required. Extraction in vitro into an aqueous environment results in the oil floating on top of the aqueous phase containing the dissolved active. This may not be acceptable for certain in vitro applications such as diagnostic kits or automated assay systems. Finally, most of the natural, FDA-approved, oils, which can be used clinically, are vulnerable to photodegradation, oxidation or other forms of damage and require careful storage in the dark at relatively low temperatures. Additionally, they are not completely chemically inert so that they can slowly react with the suspended particles.

The Alliance Pharmaceutical Company has explored the use of powders of water-soluble substances in the remarkable new non-aqueous perfluorocarbon liquids (Kirkland WD Composition and method for delivering active agents. U.S. Pat. No. 5,770,181. (1995)). This patent is primarily concerned with the function of the PFCs as oral contrast enhancing agents for diagnostic imaging of the intestines. The water-soluble powders exemplified therein were added to improve the palatability or the enhancement of the contrast effect in the gastrointestinal tract of the PFCs. However, Kirkland perceptively realized that these liquids could also be used for drug delivery although there are no examples given. In particular, only shelf stable commercially available powders are exemplified in the patent. We have now found that fragile actives stabilized in sugar glass microspheres can be engineered to produce extremely stable two-phase PFC liquid formulations for both oral and parenteral delivery. This greatly extends the utility of the Kirkland patent to the delivery of parenteral drugs and vaccines in ready-to-inject formulations that require no refrigeration of any kind. Of particular value is the discovery that the low viscosity, high density and low surface tension of PFCs means that these stable suspensions can be delivered by automatic devices such as liquid jet injectors. This opens up two important additional fields to this technology namely mass immunization campaigns and also self injection.

Perfluorocarbons (PFCs) are novel, extremely stable liquids produced by the complete fluorination of certain organic compounds. They cannot be classified as either hydrophilic or lipophilic, as they are in fact essentially immiscible with both oil and water or any other solvent whether polar or non-polar, except other PFCs. (Reviewed in Krafft M P & Riess J G. "Highly fluorinated amphiphiles and colloidal systems, and their applications in the biomedical field. A contribution." *Biochimie* 80 489–514 1998). Furthermore, they do not participate in hydrophobic interactions with oils nor hydrophilic interactions with water or hydrophilic materials. As a consequence gross phase separation, as seen when hydrophilic particles clump strongly together in oil, tends not to occur in PFCs. They may not require surfactants to produce stable suspensions, but fluorohydrocarbon (FHC) surfactants are available (Krafft & Riess 1998) and are active at minute concentrations in PFC liquids. At these very low concentrations FHC surfactants can ensure perfect monodisperse systems of certain particles which show a tendency to aggregate in their absence. The PFC liquids themselves are chemically completely non-reactive and the lower molecular weight types do not accumulate in the body but, being volatile, are eventually exhaled in the breath.

Because they are excellent solvents for gases, PFCs have already been used in large quantities in very special clinical applications. Their ability to exchange carbon dioxide for dissolved oxygen is better than that of haemoglobin. This was first demonstrated in "bloodless rats" by R. P. Geyer in 1968 (Geyer R P, Monroe R G & Taylor K. "Survival of rats totally perfused with perfluorocarbon-detergent preparation." in: *Organ Perfusion and Preservation*, J. V Norman, J Folkman, L. E. Hardison, L. E Ridolf and F. J. Veith eds. Appleton-Century-Crofts, New York. 85–95 (1968)). Perfluorooctyl bromide, in the form of a PFC-in-water emulsion and under the trade name Oxygent™ (Alliance Pharmaceutical Corp.) is presently being evaluated in humans as an alternative to blood transfusion for certain surgical procedures. PFCs have also been used by inhalation, as liquids, into the lungs as a treatment for respiratory distress syndrome in premature babies.

Their high density combined with chemical inertness has also been found to be valuable. Perfluorophenanthrene, under the trade name Vitreon™ (Vitrophage Inc.), is used to prevent collapse of the capsule of the eye during surgery and to permit repositioning of detached retinas. PFCs have also been used as contrast media for Magnetic Resonance Imaging (MRI) and for this purpose it has been reported that hydrophilic powders may be suspended in them in order to either improve their imaging properties or make them more palatable. (Kirkland W. D. "Composition and method for delivering active agents" U.S. Pat. No. 5,770,181. 1998). This patent also suggests the use of PFCs as the continuous phase for delivering particulate water-soluble drugs. Since the number of parenteral drugs, which are stable as dry powders at room temperature is limited, this patent does not have applicability to the majority of injectable drugs. However, the combination of drug stabilization in microsphere powders of sugar glasses as described in Roser and Garcia de Castro (1998) and injectable PFCs renders this technology applicable to virtually all parenteral drugs and vaccines.

SUMMARY OF THE INVENTION

The invention herein uses a two-phase system, with PFCs as the continuous phase containing a discontinuous glass phases in suspension, as drug delivery preparations. Perfluorocarbon based preparations present major advantages in that different PFCs may be blended to obtain final mixtures with densities ranging from approximately 1.5 to 2.5 g/cm$^3$. This allows for the particles to be formulated with densities matching the suspension fluid in order that they do not float or sink to the bottom of the container but remain in the form of a stable suspension. Particles therefore need not be of submicron size as required in oil based preparations to prevent sedimentation, but may vary greatly in size. The ultimate particle diameter is governed only by the purpose of the preparation. Preparations intended for needle injection or jet injection could contain particles in the range of 0.1 to 100 micrometers, or preferably 1 to 10 micrometers. This allows for a great simplification in the manner of manufacture of the particles and avoids the necessity for extremely small particle size production by milling. Particles can be made by conventional spray drying or by freeze-drying followed by simple dry or wet milling. When a high solids content in the suspension is needed it is desirable that the particles be spherical in shape. Irregularly shaped particles have a much greater tendency to "bind" together inhibiting free-flow, while spherical particles have an inherent "lubricity" enabling solids contents of well over 20% to be achieved. Such particles are easily made by spray-drying, spray-freeze-drying or emulsion solidification.

The suspended powders, if formulated appropriately, need no surfactants, producing stable suspensions from which the sugar glass particles dissolve almost instantly when shaken with water. If minor aggregation is perceived as a problem, small amounts of a FHC surfactant such as described in Krafft and Riess (1998) may be advantageously added to the PFC fluid either before or after the admixture of the stable powder. Like the PFCs, these FHCs are inherently extremely inert and non-reactive. There is thus no solvation of the particles and no chemical reaction between the suspended particles and the PFC phase. Because both the sugar glass particles and the PFC liquid are environmentally stable there is no degradation due to light, high temperatures, oxygen etc. They have negligible in vivo or in vitro toxicity and they have been extensively tested and approved by the regulatory authorities by being infused into both animals and man in large volumes for blood replacement purposes. While high molecular weight PFCs have been reported to accumulate in the liver, the lower molecular weight examples used in this application are eventually eliminated from the body in the exhaled breath.

Their low surface tension and their low viscosity enables them to flow very easily through the narrow bores which may be encountered in hypodermic needles, automated systems or liquid jet injectors. PFCs are excellent electrical insulators and therefore it is easy to achieve monodisperse suspensions of particles carrying the same small surface electrostatic charge. They are dry and completely non-hygroscopic liquids. Their very low water content maintains the dryness of the suspended powders, preventing the dissolution or degradation of the incorporated actives. Their unique lack of solvent properties make them ideal for suspending either hydrophilic or hydrophobic particles and means that the final suspensions are compatible with virtually any materials used in containers or delivery devices. This is in contrast with oil-based preparations, which can cause severe jamming of syringes for example, by swelling the rubber seals on the plungers. PFCs can be obtained in a range of densities, vapor pressures and volatilities, (Table I). Their high densities cause them to sink in most conventional buffers, allowing for easy separation from the product particles, which dissolve in the aqueous phase that floats on top. This therefore facilitates their use for in vitro applications such as diagnostics.

TABLE I

Detailed Description of the Invention
Properties of some PFCs

| Perfluoro- | MW | Density (Kg/L) | Viscosity (mPas) | Surface tension (mN/m) | Vapor pressure (mbar) |
|---|---|---|---|---|---|
| hexane | 338 | 1.682 | 0.656 | 11.1 | 294 |
| -n-octane | 438 | 1.75 | 1.27 | 16.98 | 52 |
| decalin | 462 | 1.917 | 5.10 | 17.6 | 8.8 |
| phenanthrene | 624 | 2.03 | 28.4 | 19 | <1 |

The use of PFCs as vehicles for delivery of pharmacological agents or bioactive agents was previously suggested in Kirkland (1995). This patent exemplified only inherently stable commercially available flavoring or effervescent powders and the like It contained no examples of any stabilized bioactives such as vaccines or pharmaceuticals. Furthermore it does not consider the possibility of making an injectable (parenteral) preparation by using PFCs as the suspension vehicle for the active particles. In order to achieve a stable formulation of inherently fragile biomolecules with a long shelf life using PFCs as the non-aqueous vehicle, the particles would preferably be formulated to contain a glass-forming agent capable of stabilizing the incorporated active. This may be from a variety of sugars, including trehalose, lactitol, palatinit, etc as described in PCT No. WO 91/18091 or more preferably other more effective monosaccharide sugar alcohols or glass forming agents as described in UK Pat. Application no. 9820689.9.

In order to prevent the particles from floating in the dense PFC phase, it is advantageous to incorporate a density-regulating agent in the particles. This may be either a soluble salt such as sodium or potassium chloride or sulphate or more preferably, an insoluble material such as barium sulphate, calcium phosphate titanium dioxide or aluminum hydroxide. The insoluble, non-toxic materials are preferred since the release of large amounts of ionic salts in the body can cause considerable local pain and irritation. The insoluble materials may, in some cases, such as in vaccine preparations, be part of the active preparation as an adjuvant. The density regulator may be in solid solution in the sugar glass particles or an insoluble particulate material in suspension in the sugar glass. When correctly formulated, the sugar glass particles are approximately density matched with the PFC liquid, are buoyancy neutral, and neither float nor settle but remain in stable suspension without caking.

Because PFC liquids are good electrical insulators, with a typical resistivity of greater than $10^{13}$ ohm.cm, tiny surface charges on the suspended particles can have significant effects on suspension stability. In order to prevent the suspended particles from aggregation due to weak short-range forces, they are preferably manufactured containing an excipient such as lysine or aspartic acid capable of donating a weak residual electrostatic charge to the dry particles. This prevents aggregation by ensuring charge repulsion of the particles, similar to that seen in stable colloids. Alternatively, small amounts of FHC surfactants such as perfluorodecanoic acid may be advantageously dissolved in the PFCs to give dispersed, preferably monodisperse, suspensions.

These particles may be manufactured in a number of ways, including air, spray or freeze-drying and need not to be particularly small but may be a heterogeneous mix of sizes ranging between $0.1\mu$ and $100\mu$ in diameter. For some applications even millimeter-sized particles may be suitable.

The use of these stable suspensions is restricted to neither parenteral use as exemplified above nor oral use as exemplified in Kirkland (1995). Because the PFC liquid vehicle is so non-toxic and non-reactive, it is an ideal vehicle for mucosal, including intrapulmonary, intranasal, intraocular, intra rectal and intravaginal delivery. The ability, provided by this patent, to produce stable, sterile and non-irritant formulations for mucosal delivery of even very unstable drugs or vaccines is a considerable advance. Also, the very dry and completely non-hygroscopic nature of the PFC liquid greatly assists in the maintenance of sterility of these preparations during prolonged storage and intermittent use as micro-organisms cannot grow in the absence of water.

Since volatile perfluorohydrocarbons and chlorofluorocarbons have long been used as propellants in inhalers designed to achieve drug delivery to the deep lung, the stable PFC formulations described herein are ideal for generating fine mists of liquid STASIS droplets for intrapulmonary delivery. For this application, the size of the particles which constitute the discontinuous suspended phase in the PFC droplets is important and should not exceed 1 to 5 $\mu$m, preferably 0.1 to 1 $\mu$m in diameter. For delivery to other mucosal surfaces in the nose or eye, the particle size is less important and can be up to 100 $\mu$m or even several mm in diameter.

Figure 1:
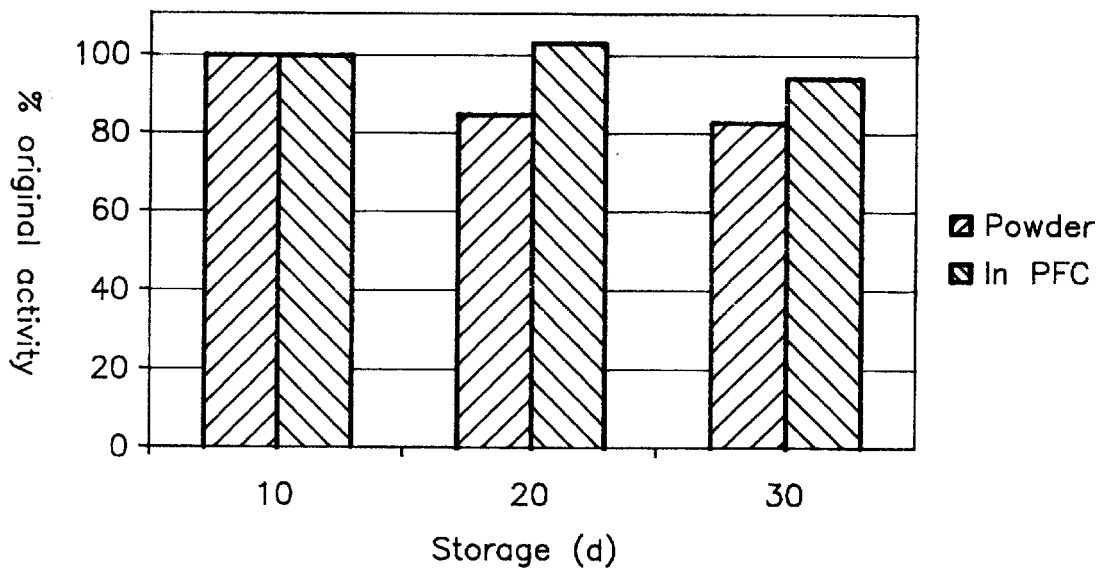
FIG. 1 Alkaline phosphatase (Sigma Aldrich Ltd.) was stabilized in a glass based on mannitol 33.3%, calcium lactate 33.3% and degraded gelatin 33.3% (Byco C, Croda Colloids Ltd.), spray dried as microspheres and stored at 55° C. either as dry powder or as a stable suspension in Perfluorodecalin. The activity remained around the 100% mark (103% at 20d and 94% at 30d). There was more loss in the dry powder which was not suspended in PFC (around 80% of activity remained).
Figure 2:
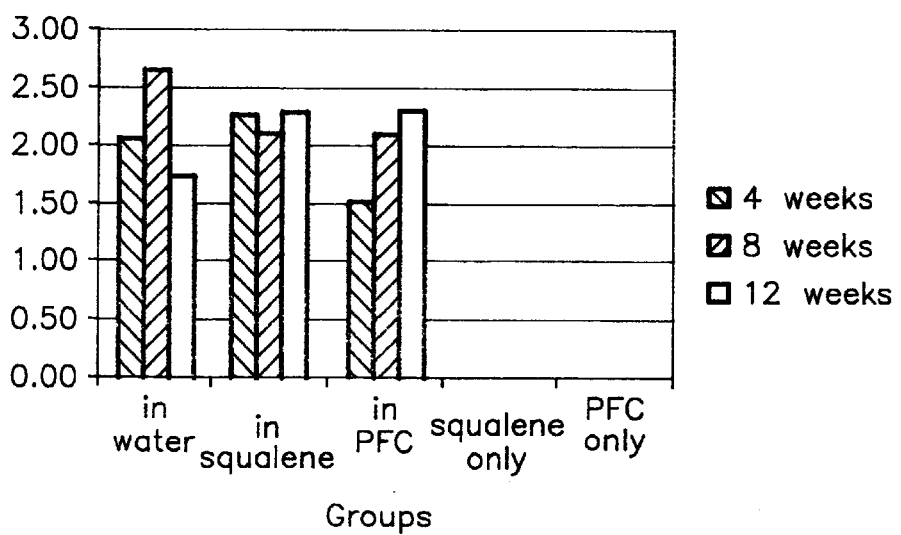
FIG. 2 A commercial tetanus toxoid vaccine, (#T022 kindly supplied by Evans Medeva plc) was formulated as a density-matched powder using added calcium phosphate in 20% trehalose solution. It was freeze-dried by spraying into liquid nitrogen using a two fluid nozzle followed by freeze drying the frozen microsphere powder in a Labconco freeze dryer with the initial shelf temperature at 40° C. throughout primary drying. The antibody response of six group of 10 Guinea Pigs was measured 4, 8 and 12 weeks after being injected with the same dose of ASSIST stabilized Tetanus Toxoid vaccine reconstituted in saline buffer or as anhydrous preparations in oil or PFC.

The responses to all the dried preparations was lower than the fresh vaccine control (not shown) indicating a significant loss of immunogenicity on spray drying. The antigenicity of the toxoid, as measured by capture ELISA, was unaltered by the drying process. This suggested that more work is required to perfect the preservation of the aluminum hydroxide adjuvant on drying.

The response to STASIS vaccine density-matched with calcium phosphate (group 3) is essentially the same as the control vaccine reconstituted in aqueous buffer (group 1) and the powder in oil vaccine (group 2) while control animals injected with the non-aqueous vehicles only (groups 4 & 5) showed no response.

DESCRIPTION OF PREFERRED EMBODIMENTS

EXAMPLE 1

Spray-dried particles in PFCs.

Particles were produced by spray drying from aqueous solution using a Labplant model SD 1 spray dryer using sugars and other excipients. Typical formulations were:

| A. | mannitol | 15% w/v |
| | calcium lactate | 15% w/v |
| | in water | |
| B. | trehalose | 15% w/v |
| | calcium phosphate | 15% w/v |
| | in water | |

The particles were produced using a two-fluid nozzle with a liquid orifice of 0.5 mm internal diameter. A half-maximum nozzle airflow was found optimal and the drying chamber operated at an inlet temperature of 135° C. and an outlet temperature of 70–75° C. The particles were collected in a glass cyclone and subjected to secondary drying in a vacuum oven using a temperature ramp to 80° C. over 4 hours. On cooling they were suspended in PFC using ultrasound. Either a 30 second burst of ultrasonic energy from a titanium probe in an MSE MK 2 ultrasonic cabinet operating at about 75% power or immersion in a Decon FS200 Frequency sweep Ultrasonic bath for up to 10 minutes was found to be sufficient.

The resulting suspension was monodisperse and consisted of spherical glass particles ranging in size from about 0.5 to 30μ with a mean of about 10μ as judged microscopically. The mannitol/calcium lactate particles rose to the top of the PFC layer over several minutes but could readily be resuspended with gentle shaking. The trehalose/calcium phosphate particles were almost density matched with the PFC and formed a stable suspension.

Spray dried powders of sugar glass particles were suspended in perfluorohexane, perfluorodecalin and perfluorophenanthrene at 1, 10, 20 and 40% w/v. They were found to give monodisperse suspensions with little tendency to aggregate. The addition of 0.1% perfluorodecanoic acid to the PFC inhibited any slight tendency to aggregate on surfaces. These suspensions were found to pass easily through a 25 g needle by aspiration or ejection.

EXAMPLE 2

Stability of suspension of glass stabilized enzyme in PFC

Alkaline phosphatase (Sigma Aldrich Ltd.) was spray dried in a Labplant machine as above. The formulation contained mannitol 33.3% w/w, calcium phosphate 33.3% w/w and degraded gelatin (Byco C, Croda colloids Ltd.) 33.3%. The dried enzyme was stored at 55° C. either as the dry powder or as a suspension in perfluorodecalin. The enzyme formulated in these microspheres consisting of a Mannitol-based glass suspended in perfluorodecalin show retention of close to 100% of enzyme activity for more than 30 days at 55° C. (FIG. 1).

EXAMPLE 3

Efficacy in vivo

Pre clinical trials of a similar formulation containing a clinical tetanus toxoid vaccine (kindly supplied by Medeva plc) were undertaken in collaboration with the National Institute of Biological standards and Control (an approved laboratory of the World Health Organization). The results from this trial showed that the stable STASIS preparation was completely equivalent to a water-based liquid vaccine in its ability to immunize guinea pigs to develop a protective serum antibody response (FIG. 2). This confirmed that the suspension in PFC constituted a ready-to-inject formulation with the same bioavailability in vivo as a conventional water based liquid formulation.

EXAMPLE 4

Spray-freeze-dried particles

Particles were also made by spraying liquid droplets into liquid nitrogen and then vacuum-drying the frozen powder. These particles were less dense than the spray dried powders and formed pastes in PFCs at concentrations higher than 20% w/v. At lower concentrations they formed monodisperse suspension after sonication.

Typical formulations used were

| | substance | final concentration w/w |
|---|---|---|
| A. | Trehalose | 100% |
| B. | Trehalose | 50% |
| | Calcium phosphate | 49.5% |
| | Aluminum hydroxide | 0.5% |

EXAMPLE 5

Milled hydrophobic particles

The hydrophobic sugar derivatives sucrose octaacetate and trehalose octaacetate readily form glasses when either quenched from the melt or dried rapidly from solution of chloroform or dichloromethane. Their use has been described as controlled release matrices for drug delivery (Roser et al "Solid delivery systems for controlled release of molecules incorporated therein and methods of making same" PCT Pub No WO 96/03978 1994)

A trehalose octaacetate powder was made by melting in a muffle furnace and quenching the melt on a stainless steel plate. The resultant glass disks were ground in a pestle and mortar and then in a high-speed homogenizer to produce a fine powder. This was suspended in perfluorohexane, perfluorodecalin and perfluorophenanthrene at 1 and 10% w/v. They were found to give well dispersed suspensions. These suspensions were found to pass easily through a 23 g needle.

EXAMPLE 6

Reconstitution in aqueous environments

Because of the nature of the soluble sugar glass particles and the properties of the PFCs it was anticipated that actives in these suspensions would release rapidly in the body. In order to demonstrate complete release of an included active substance, particles were formulated to contain:

| | |
|---|---|
| Trehalose | 20% w/v |
| Calcium lactate | 20% w/v |
| Lysine | 0.5% w/v |
| Mordant Blue 9 dye | 1% w/v |

The formulation was spray dried as above and added to perfluorophenanthrene and perfluorodecalin to produce 20% w/v dark blue, opaque suspensions. Upon addition of water to an equal volume of the suspensions and shaking, it was found that virtually all of the blue dye was released into the water phase which formed a clear blue layer floating on the nearly colorless PFC with a clean sharp interface between them.

EXAMPLE 7

Non reactivity between particles in suspension

Because the individual microspheres in a PFC suspension are physically isolated from all other particles, potentially reactive substances can be present together in the same suspension in separate particles without any danger of them interacting. When the sugar glass is dissolved and the molecules can come together, the reaction occurs.

In order to demonstrate this, a suspension was made to contain two types of particles, one (a) with the enzyme alkaline phosphatase and the other (b) with its colorless substrate, paranitrophenyl phosphate Formulations were:

| | | |
|---|---|---|
| a) | Trehalose | 10% w/v |
| | Sodium sulphate | 10% w/v |
| | Alkaline phosphatase | 20 U/ml |
| | In 5 mM Tris/HCl buffer pH 7.6 | |
| b) | Trehalose | 10% w/v |
| | Sodium sulphate | 10% w/v |
| | Paranitrophenyl phosphate | 0.44% w/v |

In 100 mM Glycine buffer pH 10.2 containing 1 mM each of $Zn^{++}$ and $Mg^{++}$ Chloride A suspension of the powders in perfluorodecalin containing 10% w/v of powder "a" and 10% w/v of powder "b" was found not to develop any color reaction but to remain as a white suspension for 3 weeks at 37° C.

Upon the addition of water and shaking, the powders dissolved in the overlying aqueous phase. The enzyme reaction took place in a mater of minutes, producing an intense yellow color of p-nitrophenol, both in the freshly prepared sample and in that which had been kept at 37° C. for 3 weeks.

EXAMPLE 8

Product release in model "tissue space"

In order to illustrate the possible behavior of PFC suspensions when injected in vivo, a model, transparent, hydrated tissue space was prepared by casting 0.2% agarose gels in polystyrene bijoux bottles. 0.1 ml of the perfluorodecalin suspension from example 5 was injected through a 25 g needle into the agarose gel. This produced a flattened white sphere of the suspension. Over the next 5–10 minutes the white color cleared from the bottom of the sphere upwards leaving a clear sphere of PFC behind. As the enzyme and substrate were released by the dissolution of the glass particles, they reacted together producing a yellow color of p-nitrophenol, which then diffused throughout the agarose over the next 1 hr.

EXAMPLE 9

Density matching.

Sugar glass particles (i.e. trehalose) obtained by either of the conventional drying methods show typical densities around 1.5 $g/cm^3$. The Perfluorocarbons we tested typically have densities ranging from 1.68 to 2.03 $g/cm^3$ (Table I). For this reason when formulated into a suspension, sugar glass particles tend to float on the PFC layer, leading to a preparation in which the active is not homogeneously distributed. Powders may however be modified in order to produce a stable suspension in PFC in which they have neutral buoyancy and neither settle nor float. This may be achieved through the addition of high-density materials prior to particle formation. These may be water soluble or insoluble.

Non water-soluble materials

Tricalcium orthophosphate has a density of 3.14 $g/cm^3$, is approved as an adjuvant for vaccines and is practically insoluble in water. Powders made to contain around 50% calcium phosphate show an increased density around 2 $g/cm^3$ and at 20% solids form stable suspensions in perfluorophenanthrene.

Examples of powders which at 20% solids in PFCs form stable suspensions include:

1 in perfluorodecalin

| | substance | final concentration w/w |
|---|---|---|
| A. | Trehalose | 50% |
| | Calcium phosphate | 50% |
| B. | Trehalose | 47.5% |
| | Calcium lactate | 10.0% |
| | Calcium phosphate | 42.5% |

2 in perfluorophenanthrene:

| substance | final concentration w/w |
|---|---|
| Mannitol | 18.2% |
| Inositol | 18.2% |
| Calcium lactate | 18.2% |
| Calcium phosphate | 45.4% |

Other density increasing non water-soluble materials, which have been used, include barium sulphate and titanium dioxide. Any non-toxic and insoluble material with the appropriate density can be used.

Water soluble materials

Soluble salts such as sodium sulphate with a density of 2.7 $g/cm^3$ may also be used as a density-increasing agent. The following powder formed stable suspensions in perfluorodecalin:

| substance | final concentration w/w |
|---|---|
| Trehalose | 50% |
| Sodium sulphate | 50% |

Other non-toxic high-density water soluble materials can also be used. These formulations have been found to cause discomfort after subcutaneous injection in guinea pigs, possibly because of the rapid dissolution of high concentrations of ionic salt.

EXAMPLE 10

Effect of density matching on actives in suspensions

Certain vaccines are formulated adsorbed on to insoluble gels or particles which act as adjuvants. Aluminum hydroxide and calcium phosphate are extensively used for this purpose. These insoluble adjuvants may themselves be used to increase the density of the particles to be suspended. In this case the high-density material is not completely inert but in fact adsorbs the active macromolecule from solution. It is necessary to demonstrate that this adsorption does not denature the active. To test this, alkaline phosphatase was used as a model active/vaccine.

The following solution was made

| | | |
|---|---|---|
| Adjuvant grade calcium phosphate | 10% w/v | (Superphos Kemi a/s) |
| Trehalose | 10% w/v | |
| $ZnCl_2$ | 1 mM | |
| $MgCl_2$ | 1 mM | |

| | -continued |
|---|---|
| Alkaline phosphatase | 20 U/ml |
| In 5mM Tris HCl buffer pH 7.6 | |

The solution was then well mixed for 10 minutes at 37° C. to allow the alkaline phosphatase to be adsorbed by the calcium phosphate. This change in absorption per minute was measured by centrifuging the calcium phosphate, sampling the supernatant and measuring its enzyme kinetics using p-nitrophenyl phosphate as substrate and a wavelength of 405 nm. The solution was spray-dried to produce a fine powder. Any desorption of the enzyme after rehydration of the powder was measured in the supernatant as above. The powder was suspended at 20% w/v in perfluorophenanthrene and found to produce a stable suspension.

| Sample tested | $d^{absorbance}$/min. (405 nm) |
|---|---|
| Original solution (25 μl) | 0.409 |
| Supernatant from above (25 μl) | 0.034 |
| Rehydrated powder (25 μl of a 20% w/v in water) | 0.425 |
| Supernatant from above (25 μl) | 0.004 |
| 20% w/v powder in perfluorodecalin (25 μl) | 0.430 |

The experiment demonstrates:
  The density of the particles may be matched to that of the PFC vehicle by the inclusion of the adjuvant calcium phosphate.
  No significant desorption or loss of enzyme activity takes place during the formulation process.

EXAMPLE 11

A STASIS preparation of the mannitol base glass as in example 1 was suspended in perfluorodecalin and loaded into a surgically clean, pump-action, polypropylene atomizer which is normally used clinically to deliver oxymetazoline nasal decongestant (Sudafed, Warner Lambert). Two sprays of the suspension were delivered into each nostril of a human volunteer who were asked to comment on the degree of discomfort experienced. The volunteer reported no discomfort at all. There was no observable side effects of the administration.

What is claimed is:

1. A composition for delivering a stable, bioactive compound to a subject comprising a first component and a second component, said first component comprising microparticles of sugar glass, metal carboxylate glass or a phosphate glass containing said bioactive agent, wherein said sugar glass, metal carboxylate glass or phosphate glass optionally includes a glass formation facilitator compound, and said second component consisting of at least one biocompatible liquid perfluorocarbon in which said first component is insoluble and dispersed, wherein said liquid perfluorocarbon optionally includes a surfactant.

2. The composition according to claim 1, wherein said sugar glass is formed from a sugar selected from the group consisting of trehalose, sucrose, raffinose, stachyose, glucopyranosyl sorbitol, glucopyranosyl mannitol, palatinit, lactitol, a monosaccharide alcohol or sugar molecules modified by the addition of hydrophobic side chains selected from the group consisting of sucrose octaacetate or trehalose octaacetate.

3. The composition according to claim 1, wherein said phosphate glass or carboxylate glass is produced from mixtures of divalent metal phosphates or metal carboxylates.

4. The composition according to claim 1, wherein said optional glass formation facilitator is selected from the group consisting of a peptide, a protein, dextran, polyvinylpyrollidone, borate ion, calcium lactate, sodium polyphosphate, and silicate or acetate salts.

5. The composition according to claim 1, wherein said sugar glass microparticles 25 are from about 0.1 to about 100 micrometers in diameter.

6. The composition according to claim 5, wherein said diameter range is from 1 to 10 micrometers.

7. The composition according to claim 1, wherein said microparticles have a water content of no more than 4% and preferably less than 2% and ideally less than 1%.

8. The composition according to claim 1, wherein said first component is monodispersed in said second component.

9. The composition according to claim 1, wherein the concentration of said first component in said second component is from about 1% to about 40% by weight.

10. The composition according to claim 9, Wherein said concentration range is 10% to 15%.

11. The composition according to claim 1, wherein said surfactant concentration in said second component ranges from about 0.01% to about 10%.

12. The composition according to claim 11, wherein said concentration is about 1%.

13. The composition according to claim 1, further comprising first component microparticles to which is added an inorganic salt in an amount effective to produce in said microparticles a density matching that of said second component liquid phase.

14. The composition according to claim 1, further comprising the incorporation into said microparticles of an excipient that confers upon said microparticles a weak residual electrostatic charge such that said microparticles repel one another.

15. The composition according to claim 14, wherein said excipient is an amino acid.

16. The composition according to claim 1 wherein said perfluorocarbon is selected from a group consisting of perfluorohexane, perfluorodecalin and perfluorophenanthrene.

17. The composition according to claim 1, wherein said bioactive compound is a vaccine, a drug, an enzyme or a diagnostic reagent.

18. A method for delivering a bioactive substance to a subject patient, comprising the steps of:

(a) producing first component microparticles according to claim 1;
  (b) suspending said microparticles in said second component perfluorocarbon according to claim 1; and
  (c) administering said admixture to said patient.

* * * * *